United States Patent [19]

Scherrer et al.

[11] Patent Number: 4,464,536

[45] Date of Patent: Aug. 7, 1984

[54] ENAMINES, PHARMACEUTICAL COMPOSITIONS, METHODS, SYNTHETIC PROCESSES AND INTERMEDIATES

[75] Inventors: Robert A. Scherrer, White Bear Lake; George G. I. Moore, St. Joseph, both of Wis.

[73] Assignee: Riker Laboratories, Inc., St. Paul, Minn.

[21] Appl. No.: 439,613

[22] Filed: Nov. 5, 1982

[51] Int. Cl.$^3$ ............................................ C07D 417/06
[52] U.S. Cl. ...................... 546/213; 546/284; 548/336; 548/374; 548/527; 549/75; 549/77; 549/78; 549/79; 544/146; 544/379
[58] Field of Search ............... 546/284, 213; 548/374, 548/336, 527; 549/77, 75, 78, 79; 544/60, 146, 379; 424/267, 246, 248.51, 250, 273 R, 273 P, 275, 274

[56] References Cited

U.S. PATENT DOCUMENTS 4,128,664 12/1978 Moore ................................. 424/324
4,172,082 10/1979 Moore ................................. 549/72
4,357,345 11/1982 Moore ................................. 549/501

FOREIGN PATENT DOCUMENTS 59090 9/1982 European Pat. Off. ............ 548/154

Primary Examiner—Robert T. Bond

Attorney, Agent, or Firm—Donald M. Sell; James A. Smith; Robert W. Sprague

[57] ABSTRACT

Antiinflammatory compounds of the following formula are disclosed:

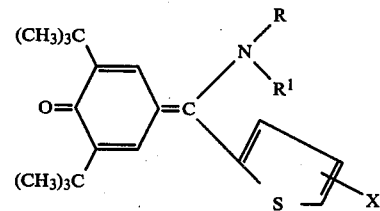

wherein R is lower alkyl; $R^1$ is selected from the group consisting of lower alkyl, benzyl, and N,N-dimethylaminoethyl; or R and $R^1$ are fused to form an optionally-substituted five- or six-membered heterocyclic ring; and X is hydrogen, methyl or halogen; and pharmaceutically acceptable acid addition salts thereof. Pharmaceutical compositions containing the antiinflammatory compounds and methods of using the antiinflammatory compounds are also described as are a synthetic process and synthetic intermediates for preparing the antiinflammatory compounds.

16 Claims, No Drawings

ENAMINES, PHARMACEUTICAL COMPOSITIONS, METHODS, SYNTHETIC PROCESSES AND INTERMEDIATES

TECHNICAL FIELD

This invention relates to enamines which are antiinflammatory agents. More specifically it relates to compounds which contain a thiophene ring, a bis(tertiary-butyl)quinone group and an amine group all bonded to a central olefinic carbon atom. The thiophene ring is optionally substituted and the amine group is optionally part of a heterocyclic ring. Also included within the scope of the invention are methods for the use of the compounds of the invention, pharmaceutical compositions containing the compounds, novel synthetic intermediates and synthetic processes for the preparation of the final compounds.

BACKGROUND OF THE INVENTION

U.S. Pat. No. 4,172,082 describes 3,5-bis(t-butyl,-4-hydroxybenzoyl-substituted thiophenes which exhibit antiinflammatory activity and are useful as stating materials for preparation of the compounds of the invention.

DETAILED DESCRIPTION OF THE INVENTION

This invention relates to enamines which are active antiinflammatory agents. The invention also relates to a method for combatting inflammatory processes in mammalian animals by administering thereto an effective amount of such a compound and to antiinflammatory compositions comprising an effective amount to such a compound and a pharamaceutically acceptable carrier. The invention also relates to processes and intermediates for preparing the compounds.

Specifically, this invention relates to enamines of the formula

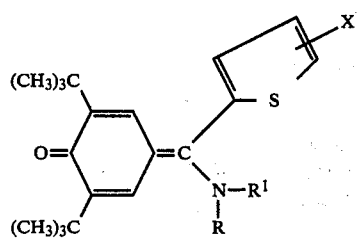

I wherein R is lower alkyl; $R^1$ is selected from the group consisting of lower alkyl, benzyl, and 2-(N,N-dimethylamino)-ethyl; or R and $R^1$ are fused to form an optionally-substituted five- or six-membered heterocyclic ring; and X is hydrogen, methyl or halogen; and pharmaceutically acceptable acid addition salts thereof.

"Lower alkyl" as used herein refers to an alkyl group containing one to six carbon atoms in straight or branched-chain configuration. Preferred lower alkyl groups contain one to four carbon atoms, and most preferred lower alkyl groups contain one or two carbon atoms.

Compounds of the invention wherein X is hydrogen are presently preferred. Compounds of the invention wherein $R^1$ is lower alky, benzyl or together with R forms a five- or six-membered heterocyclic ring are presently preferred.

Heterocyclic rings formed by R and $R^1$ may be fully saturated or may be unsaturated. Examples of fully saturated rings (which include the N atom of Formula I) are pyrrolidinyl, piperidinyl, piperazinyl, prolyl,

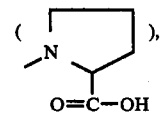

morpholinyl, N-lower alkylpiperazinyl, thiomorpholinyl and the like. Examples of unsaturated rings are pyrrolyl, imidazolyl, pyrazolyl and the like. It is presently preferred that the heterocyclic ring is fully saturated. The most preferred rings are pyrrolidinyl and piperidinyl.

The heterocyclic ring formed by R and $R_1$ is optionally substituted, and the substituent is preferably lower alkyl and most preferably methyl.

Presently preferred compounds of the invention are:
2,6-di-tert-butyl-4-[alpha-(1-piperidino)-alpha-(2-thienyl)]methylidene-2,5-cyclohexadien-1-one
2,6-di-tert-butyl-4-[alpha-(N,N-dimethylamino)-alpha-(2-thienyl)]methylidene-2,5-cyclohexadien-1-one 2,6-di-tert-butyl-4-[alpha-(N,N-diethylamino)-alpha-(2-thienyl)]methylidene-2,5-cyclohexadien-1-one
4-[alpha-(N-benzyl-N-methylamino)-alpha-(2-thienyl)-]methylidene-2,6-di-tert-butyl-2,5-cyclohexadien-1-one
2,6-di-tert-butyl-4-[alpha-(1-pyrrolidinyl)-alpha-(2-thienyl)]methylidene-2,5-cyclohexadien-1-one The compounds of the present invention may be prepared according to the following reaction sequence, Process I:

PROCESS I

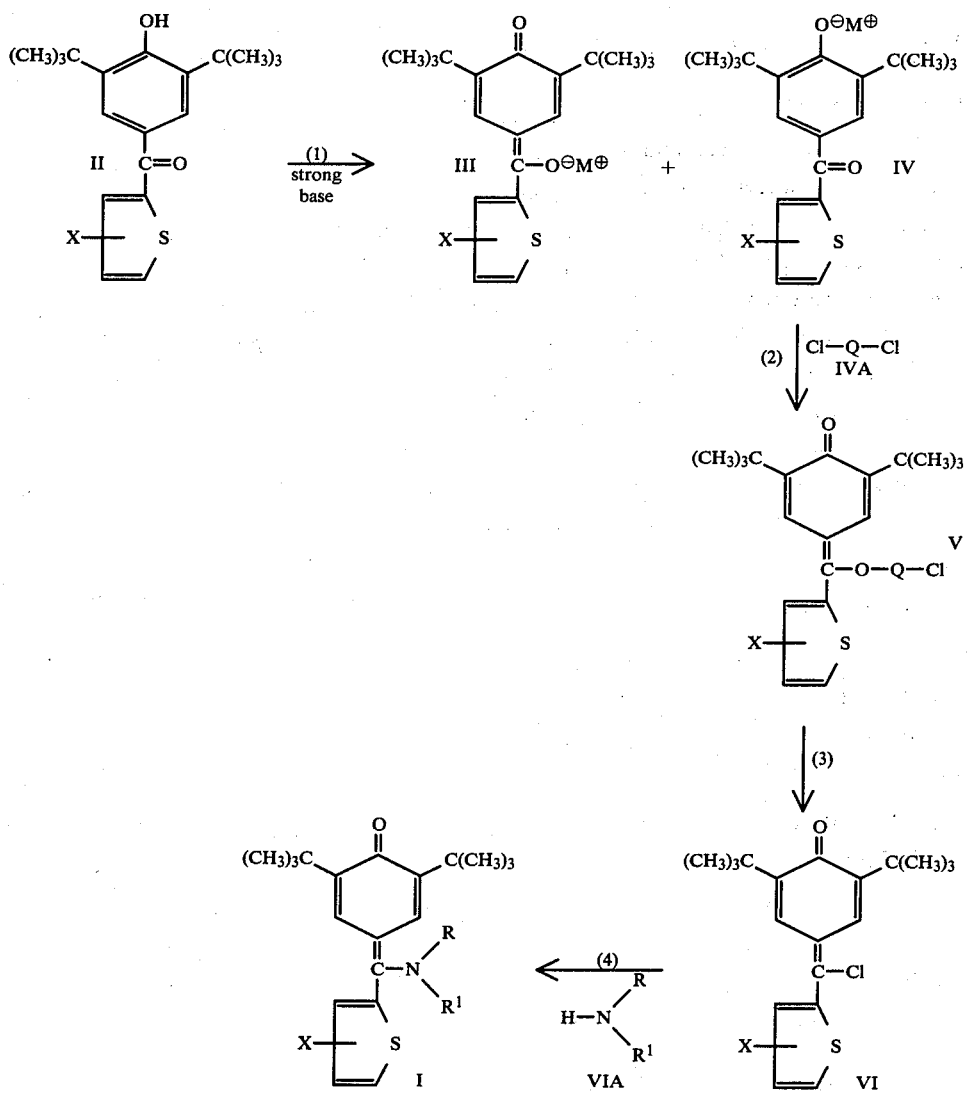

wherein R, R¹ and X are as defined previously; M is lithium, sodium or potassium; and Q is

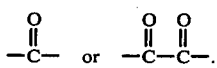

Step (1) of Process I requires the reaction of a ketone of Formula II with a strong base such as sodium or potassium hydride or n-butyl lithium to provide the novel metal salt of Formula III and/or Formula IV, these formulas representing resonance structures. Ketones of Formula II may be prepared in accordance with the procedures described in U.S. Pat. No. 4,172,082 (Moore), incorporated herein by reference. The red-orange color of the salts indicates that resonance Formula III predominates. The fact that subsequent reaction of the salt occurs predominantly at the carbonyl oxygen is currently attributed to steric shielding of the phenolic oxygen atom. The site of the predominant reaction is surprising, however, since a similar reaction with 2,6-di-tert-butyl-4-methylphenol is reported to proceed smoothly on the phenolic oxygen and reaction at the cabonyl oxygen entails loss of aromaticity. For purposes of subsequent discussion we refer to the salt as being of structure III above.

The reaction of step (1) is carried out in an inert solvent such as glyme, tetrahydrofuran, benzene or the like. It may be desirable to conduct the reaction in an inert atmosphere, e.g., under nitrogen. The reactionoccurs at moderate temperatures such as 0° to 100° C. The salts generally are not isolated, but are used directly in step (2).

In step (2) a suitable organic chlorine source is reacted with the metal salt of Formula III. Suitable chlorine sources of the formula IVA include phosgene

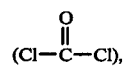

oxalyl chloride

The compounds of the present invention may also be prepared according to the following reaction sequence, Process II:

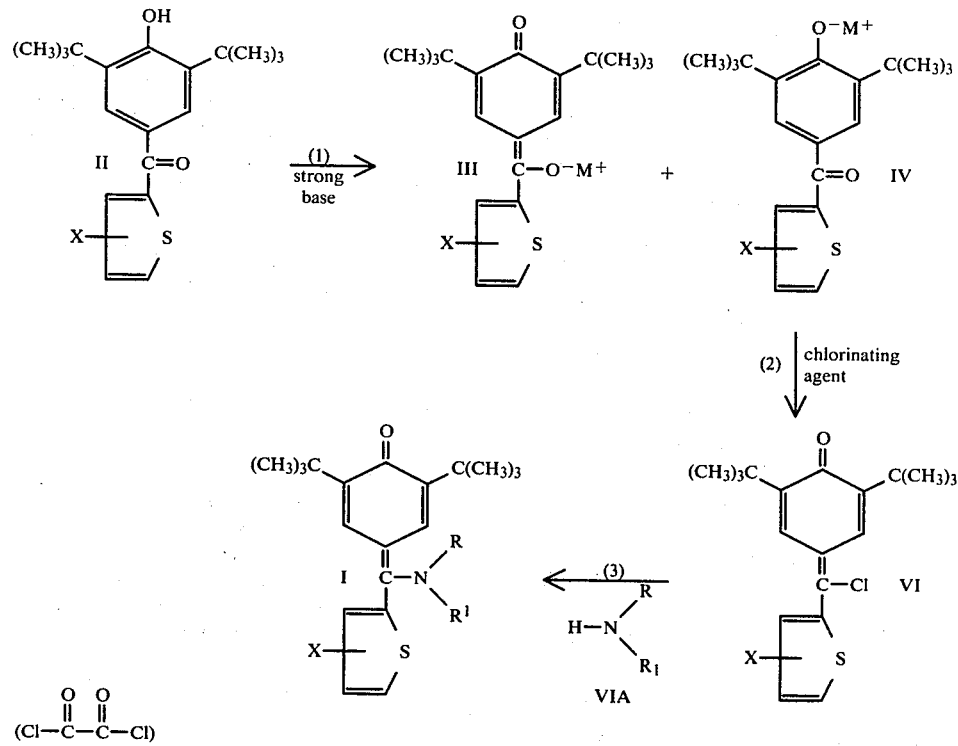

and the like. The novel product of Formula V is generally not isolated, but is used as is directly in step (3). The reaction temperature of step (2) is generally about 0° C. The solvent is most conveniently the same inert solvent employed in step (1).

In step (3) the intermediate of Formula V is converted to the novel intermediate of Formula VI. The conversion is generally carried out by heating the solution of the intermediate of Formula V obtained from step (2) at or slightly below its reflux temperature. The course of the reaction is conveniently followed by chromatographic analysis. When all of the intermediate of Formula V has been converted to the intermediate of Formula VI the reaction mixture is cooled and the product is isolated. The intermediate of Formula VI is generally an orange-red to red-colored solid when purified, although it is generally isolated and employed in step (4) as an oil. Isolation and purification may be carried out by column or high pressure liquid chromatography.

The reaction of step (4) is carried out by first dissolving the intermediate of Formula VI in an inert solvent such as diethyl ether or (Preferably) tetrahydrofuran and then adding an amine of the formula VIA. Depending on the amine employed, it may be necessary to heat the reaction mixture at its reflux temperture to obtain a satisfactory reaction rate. Pyrrolidine reacts readily at a temperature of 20° C. and heating is therefore generally not required. The reaction of step (4) may be monitored chromatographically. The compound of Formula I is readily isolated as a solid by conventional methods.

wherein R, $R^1$, M and X are as defined previously.

In step (1) of Process II, the ketone of Formula II is reacted with a strong base to provide the metal salt of Formula III and/or formula IV in accordance with Step (1) of Process I.

The metal salt of Formula III is then transformed in Step (2) directly to the intermediate of Formula VI by reacting the metal salt with an inorganic chlorine source such as thionyl chloride or phosphorous pentachloride. The reaction temperature will generally be between about 0° C. and the reflux temperature of the mixture. Since phosphorus pentachloride is a solid, an inert solvent is used when it is chosen as the chlorine source.

In Step (3) the intermediate of Formual VI is reacted with an amine of Formula VIA in accordance with Step (4) of Process I to provide the compound of Formula I.

The compounds of the present invention may also be prepared according to the following reaction sequence, Process III:

Process III

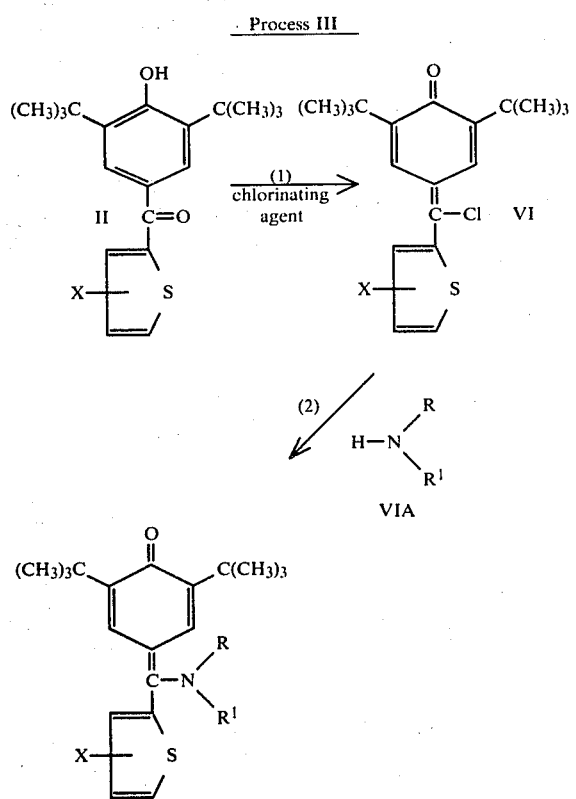

wherein R, R[1] and X are as defined previously.

In Step (1) of Process III the ketone of Formula II is reacted directly with a strong chlorinating agent such as thionyl chloride or phosphorus pentachloride to provide the intermediate of Formula VI. When the chlorinating agent is phosphorus pentachloride, the reaction is preferably conducted in an inert solvent such as benzene or toluene. When the chlorinating agent is thionyl chloride, it is preferred that no solvent be employed and it is also preferred that a small amount (e.g., generally less than 1% by volume is sufficient) of N,N-dimethylformamide be used as a catalyst. When the solvent is used with thionyl chloride it should be an inert organic solvent such as benzene, toluene, chloroform and the like. The reaction temperature will generally be between about 20° C. and the reflux temperature of the mixture. Care must be used to avoid hydrolysis of the intermediate of Formula VI since hydrogen chloride by-product may catalyze hydrolysis of that intermediate in the presence of water.

In Step (2) the intermediate of Formula VI is reacted with preferably about an equimolar amount of an amine of Formula VIA in accordance with Step (4) of Process I to provide the compound of Formula I.

In the case of weakly basic amines such as pyrrole and imidazole, the amine of Formula VIA may be in the form of an alkali metal salt.

Acid addition salts of compounds of the invention are readily prepared by reaction of compounds of Formula I with various pharmaceutically acceptable acids, e.g., hydrochloric, hydrobromic, acetic, phosphoric acids and the like.

The antiinflammatory activity of compounds of the inventioncan be conveniently demonstrated in aminals using well-known test methods.

The assay employed in determining the antiinflammatory activity of the compounds of the invention is a combination of a carrageenan-included rat paw edema rection and a reversed passive cutaneous Arthus reaction in the same animal.

The carrageenan-induced rat paw edema model is a standard laboratory assay used to predict classical "aspirin-like" antiinflammatory activity. The carrageenan-induced paw edema technique employed in determining the antiinflammatory activity of the compounds of the invention is a modification of that described by Winter et al. (Proc. Soc. Exp. Biol. Med. III, 544–547, 1962). The edema is measured by mercury displacement using a Stratham ® pressure transducer which is connected to a strain gauge coupler in a Beckman Type RS Dynograph recorder. A permanent ink recording is obtained.

Generally, the reversed passive cutaneous Arthus reaction identifies agents which affect one or more of the following factors: antigen-antibody complexes, complement and infiltrating polymorphonuclear neutrophil leukocyctes (PMN's). The reversed passive Arthus reaction employed in determining the antiinflammatory activity of the compounds of the invention is a modification of an assay described by Goldlust et al. (The Recognition of Anti-Rheumatic Drugs, D. E. Dumonde and M. K. Jasnai, eds., MTP (London), pp. 119–136, 1977). Anti-rat serum was chosen to induce the Arthur lesion since it contains antibodies against the rat's own serum proteins and only one injection is therefore necessary to produce the lesion.

The assay employed in determining the anti-inflammatory activity of the compounds of the invention is described in greater detail below.

Male rates (ARS/Sprague/Dawley), weighing 100-200 g, are administered test compounds or vehicle, p.o., one hour before the intradermal injection of goat anti-rat serum and intraplantar injection of a suspension of carrageenan. Treatment doses are selected in most cases as a function of their acute oral approximate lethal dose 50 ($ALD_{50}$). These values are obtained by the administration of graded doses at 0.3 log intervals to groups of four mice. The reactions to the carrageenan and antiserum are evaluated three and four hours later, respectively. The vehicle for orally administered drugs is 4% aqueous acacia and is administered in a volume of 0.5 ml/100 g body weight. Each treatment group comprises six rats.

The edema is induced by the intraplantar. injection of 0.1 ml of a 0.5% suspension of carrageenan (Seakem 402, Marine Colloids, Inc.) in 0.9% saline into one hind paw. The other hind paw is injected with 0.1 ml of 0.9% saline solution. The volumes of both hind paws are determined three hours later by displacement of mercury (ml). The difference in volume between the carrageenan-injected and saline-injected paws is recorded. Percent inhibition of the increase in volume which occurs in a control group of rats (vehicle-treated) is determined for each group. The statistical significance of any difference is determined by Student's T-test (one-tailed).

The Arthus reaction is induced by the intradermal injection into an unshaven site on the dorsal midline of of 0.1 ml of reconstituted goat anti-rate serum (Cappel Labs). Four hours after intradermal challenge the rats are killed by asphyxiation (exposure to dry ice vapor) and the skin is reflected. The cutaneous Arthus lesion is measured as the weight in grams of a 1¼" diameter arch punch sample. Percent inhibition of the reaction as determined from comparison with a control group treated with the drug vehicle is calculated after subtracting the mean weight of 1¼" punch sample of skin from a group of rats injected intradermally with normal goat serum and intraplantarly with carrageenan. The presence or absence of hemorrhage in the lesion is also noted. The statistical significance of any difference is determined by Student's T-test (one tailed).

The compounds of the invention are preferably administered orally but other known methods of administration can also be used, e.g., dermatomucosal administration (for example dermally, rectally and the like), parenteral administration (for example by subcutaneous injection, intramuscular injection, intraarticular injection, intravenous injection, and the like), and ocular administration. Effective dosages should be less than a toxic amount. Such dosages ordinarily are within the range of about 1 to 500 mg of the compound of the invention per kg of body weight of the mammal to be treated. Oral dosages are usually below 100 mg/kg. The compounds of the invention ordinarily are administered in the form of compositions containing the compound together with a pharmaceutically acceptable carrier. Suitable compositions for oral administration are in the form of liquids (such as 4 percent acacia and polyethylene glycol solutions), tablets (which can contain anhydrous lactose, microcrystalline cellulose, modified starch, calcium stearate and talc, as well as other conventional compounding agents together with the active antiinflammatory agents), solid suspensions and capsules. Pharmaceutically acceptable carriers for topical application include creams, gels, tapes and the like. Liquid formulations, such as solutions or suspensions of the active ingredient in inert carriers, can be used for dosage by injection.

Using the methods described above, the preparation of compounds of the invention is illustrated in the following non-limiting examples.

EXAMPLE 1

Preparation of 2,6-di-tert-butyl-4-[alpha-(N,N-dimethylamino)-alpha-(2-thienyl)]methylidene-2,5-cyclohexadien-1-one Part A. Step (1) of Process I A solution of 10 g (31.6 mmole) of 2,6-di(tert-butyl)-4-(2'-thenoyl)phenol in 150 ml of tetrahydrofuran which has been dried over calcium hydride and stabilized with 0.25% 2,6-bis(tert-butyl)-4-methylphenol was prepared. To this solution was added 1.5 g of a 60% by weight mixture of sodium hydride in oil. A red-orange color developed. The mixture was heated to boiling and then an infrared spectrum was taken. Complete reaction was indicated by loss of the carbonyl absorption. The mixture containing the sodium enolate of 2,6-di(tert-butyl)-4-(2-thenoyl)-phenol was cooled and used in Part B below.

Part B. Steps (2) and (3) of Process I

To the mixture of Part A was added 6 ml of liquid phosgene. After dissolution was achieved, the mixture was heated at its reflux temperature for two hours. Process of the conversion of the compound of Formula V to that of Formula VI was followed by loss of absorption at 1550 cm$^{-1}$ in the infrared spectrum of the reaction mixture. Chromatography on silica gel, using carbon tetrachloride as the eluent, gave 6.0 g of a red solid, m.p. 86°–87° C., which was 4-[alpha-chloro-alpha-(2-thienyl)]methylidene-2,6-di(tert-butyl)-2,5-cyclohexadien-1-one. Analysis: Calculated for $C_{19}H_{23}ClOS$: %C, 68.1; %H, 6.9; %Cl, 10.6. Found: %C, 67.7; %H, 7.0; %Cl, 10.3. A sample of this solid was unstable under ambient conditions and decomposed (hydrolyzed) slowly over a period of one to three weeks.

Part C. Step (4) of Process I

To a solution of 6.0 g (17.9 mmole) of 2,6-di(tert-butyl)-4-[alpha-chloro-alpha-(2-thienyl)]methylidene-2,5-cyclohexadien-1-one (from Part B above) in 100 ml of tetrahydrofuran was added an excess of gaseous dimethylamine. The mixture was heated on a steam bath for two hours and then poured into an ice-water mixture. The resulting mixture was extracted with dichloromethane and the extracts were filtered and then evaporated to provide an oil. After the oil crystallized, the resulting solid was suspended in hexane. The suspension was filtered to provide red solid 2,6-di-tert-butyl-4-[alpha-(N,N-dimethylamino)-alpha-(2-thienyl)]methylidene-2,5-cyclohexadien-1-one, m.p. 193°–194° C. Analysis: Calculated for $C_{21}H_{29}NOS$: %C, 73.4; %H, 8.5; %N, 4.1. Found: %C, 73.9; %H, 8.9; %N, 3.8. The structural assignment was confirmed by infrared and nuclear magnetic resonance spectral analyses.

EXAMPLE 2

Preparation of 2,6-di(tert-butyl)-4-[alpha-(N,N-diethylamino)-alpha-(2-thienyl)]methylidene-2,5-cyclohexadien-1-one Part A. Step (1) of Process I To a mixture of 5.1 g of potassium hydride and 100 ml of glyme under a nitrogen atmosphere was added over a period of 30 seconds a solution of 10 g of 2,6-di(tert-butyl)-4-(2'-thenoyl)phenol in 80 ml of glyme. The mixture was heated to 70° to 80° C. to obtain complete reaction. The mixture containing the potassium enolate of 2,6-di(tert-butyl)-4-(2'-thenoyl)phenol was cooled and used in Part B below.

Part B. Step (2) of Process I

The solution containing product from Step A was cooled to 0° C. and 8 g (62 mmole) of oxalyl chloride was added thereto. The color changed from a red-orange color to a dull orange color and formation of potassium chloride was observed. A small sample was removed and evaporated to provide an orange-colored oil. Infrared spectral analysis of the oil indicated the presence of the desired product of Formula V wherein Q is

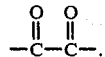

The solution was used in Part C below.

Part C. Step (3) of Process I

The solution of Part C was heated to reflux and then cooled to about 20° C. Dichloromethane (about 100 ml) was added to the solution, followed by addition of an ice-water mixture. The dichloromethane layer was separated, washed twice with water, and dried. Evaporation provided the crude intermediate of Formula VI as a red oil. The oil was dissolved in an equal volume of carbon tetrachloride and eluted through a silica gel column using carbon tetrachloride. Evaporation provided 12 g of red oil.

Part D. Step (4) of Process I

To a solution of 6.0 g (17.0 mmole) of the product from Part C in 100 ml of diethyl ether was added 5 ml of diethylamine. Heating on a steam bath for 15 minutes caused no detectable reaction. The ether was removed by evaporation and 100 ml of tetrahydrofuran was substituted therefor. After about two hours of heating on a steam bath, an additional portion (5 ml) of diethylamine was added. Heating was continued about 3 additional hours until thin layer chromatographic analysis indicated no further reaction. The mixture was poured into an ice-water mixture. This mixture was extracted with dichloromethane and the extracts were washed thrice with water and dried. Evaporation provided a deep red oil which crystallized. Recrystallization from hexane with concomitant treatment with decolorizing charcoal gave red plates of 2,6-di(tert-butyl)-4-[alpha-(N,N-diethylamino)-alpha-(2-thienyl)]methylidene-2,5-cyclohexadien-1-one, m.p. 139.5 to 140.5° C. Analysis: Calculated for $C_{23}H_{33}NOS$: %C, 74.3; %H, 9.0; %N, 3.8. Found: %C, 74.5; %H, 9.4; %N, 3.5. The structural assignment was confirmed by infrared and nuclear magnetic resonance spectral analyses.

EXAMPLE 3

Using the method of Part D, Example 2, excess N-methylbenzylamine was reacted with a 6.0 g portion of the intermediate of Formula VI (obtained in Part C, Example 2) to provide red crystals of 4-[alpha-N-benzyl-N-methyl amino)-alpha-(2-thienyl)]-2-methylidene-2,6-di(tert-butyl)-2,5-cyclohexadien-1 -one, m.p. 177°-179.5° C. Analysis: Calculated for $C_{27}H_{33}NOS$: %C, 77.3; %H, 7.9; %N, 3.3. Found: %C, 77.3; %H, 8.2; %N, 2.9. The structural assignment was confirmed by infrared and nuclear magnetic resonance spectral analyses.

EXAMPLE 4

A mixture of 5.0 g (0.0158 mole) of 2,6-di(tert-butyl)-4-(2'-thenoyl)phenol and 25 ml of thionyl chloride containing 2 drops of N,N-dimethylformamide was heated to a gentle reflux. Gas evolution was observed which continued for 1.5 hours. After gas evolution stopped, the mixture was evaporated to provide an oil. Benzene was added and the mixture was evaporated again to provide 6.6 g of 4-[alpha-chloro-alpha-(2-thienyl)]methylidene-2,6-di(tert-butyl)-2,5-cyclohexadien-1 -one as a red oil. The identity of the product was verified by infrared spectral analysis and comparison with the purified material for which a satisfactory elemental analysis had been obtained. Pure product was obtained by chromatography through silica gel using carbon tetrachloride as the eluent.

EXAMPLE 5

To a solution of 6.0 g (17.9 mmole) of 4-[alpha-chloro-alpha-(2-thienyl)]methylidene-2,6-di(tert-butyl)-2,5-cyclohexadien-1-one (from Example 4) in 100 ml of tetrahydrofuran was added a molar excess of piperidine. The mixture was heated on a steam bath for one hour, cooled and poured into water. The aqueous mixture was extracted with dichloromethane. The extracts were dried over magnesium sulfate, filtered and evaporated to provide a red residue. Trituration of the residue with hexane provided a red solid. The solid was recrystallized from a chloroform-hexane mixture to provide red crystals of 2,6-di(tert-butyl)-4-[alpha-(1-piperidino)-alpha-(2-thienyl)]methylidene-2,5-cyclohexadien-1-one, m.p. 173°-175° C. Analysis: Calculated for $C_{24}H_{33}NOS$: %C, 75.1; %H, 8.7; %N, 3.7. Found: %C, 75.3; %H, 9.0; %N, 3.4. The structural assignment was confirmed by infrared and nuclear magnetic resonance spectral analyses.

EXAMPLE 6

To a solution of 6.0 g (17.9 mmole) of 4-[alpha-chloro-alpha-(2-thienyl)]methylidene-2,6-di(tert-butyl)-2,5-cyclohexadien-1-one (from Example4) in 100 ml of tetrahydrofuran was added a molar excess of the sodium salt of imidazole (prepared from sodium hydride and imidazole in boiling tetrahydrofuran). The solution was boiled for one hour, cooled and poured into water. The aqueous mixture was extracted with dichloromethane and the extracts were dried over magnesium sulfate and filtered. Evaporation of the filtrate provided a solid residue. The residue was recrystallized from a chloroform-hexane mixture to provide 2,6-di(tert-butyl)-4-[alpha-(1-imidazolyl)-alpha-(2-thienyl)]methylidene-2,5-cyclohexadien-1-one as an orange-colored solid, m.p. 171°-173° C. Analysis: Calculated for $C_{22}H_{25}N_2OS$: %C, 72.3; %H, 6.9; %N, 7.7. Found: %C, 72.3, %H, 7.4; %N, 7.3. The structural assignment was confirmed by infrared and nuclear magnetic resonance spectral analysis.

EXAMPLES 7-12

Using the method of Example 5, the amines indicated as starting materials in the following table may be reacted with 4-[alpha-chloro-alpha-(2-thienyl)]-methylidene-2,6-di(tert-butyl)-2,5-cyclohexadien-1-one (from Example 4) to provide the following compounds of the invention.

TABLE I

| Ex. No. | Amine Starting Material | Product of Formula 1 |
| --- | --- | --- |
| 7 | triethylamine salt of proline | (structure) |
| 8 | N—methylpiperazine | (structure) |
| 9 | N—(n-butyl)-piperazine | (structure) |

TABLE I-continued

| Ex. No. | Amine Starting Material | Product of Formula I |
|---|---|---|
| 10 | thiomorpholine | (structure: 2,6-di(tert-butyl)-4-[alpha-(thiomorpholino)-alpha-(2-thienyl)]methylidene-2,5-cyclohexadien-1-one) |
| 11 | pyrrole | (structure: 2,6-di(tert-butyl)-4-[alpha-(1-pyrrolyl)-alpha-(2-thienyl)]methylidene-2,5-cyclohexadien-1-one) |
| 12 | pyrazole | (structure: 2,6-di(tert-butyl)-4-[alpha-(1-pyrazolyl)-alpha-(2-thienyl)]methylidene-2,5-cyclohexadien-1-one) |

EXAMPLE 13

Part A. Step (1) of Process I

To a suspension of 3.0 g (18.9 mmole) of potassium hydride in 25 ml of benzene was added a solution of 5.0 g (15.8 mmole) of 2,6-di(tert-butyl)-4-(2'-thenoyl)-phenol in 25 ml of benzene. The mixture was heated at its reflux temperature for 0.5 hour to provide as a bright yellow precipitate, the potassium enolate of 2,6-di(tert-butyl)-4-(2'-thenoy)phenol. This mixture was cooled to about 20° C. and used in Part B below.

Part B. Step (2) and (3) of Process I

To a stirred suspension of 15.8 mmole of the potassium enolate of 2,6-di(tert-butyl)-4-(2'-thenoyl)phenol in benzene was added a solution of 31.6 mmole of 12% by weight phosgene in benzene. The mixture was heated at its reflux temperature for about 1.5 hours and then filtered and evaporated to provide an orange-colored oil. The oil was purified by chromatography on a silica gel column using carbon tetrachloride as the eluent to provide 4-[alpha-chloro-alpha-(2-thienyl)]methylidene-2,6-di(tert-butyl)-2,5-cyclohexadien-1-one.

EXAMPLE 14

To 2.6 g of 4-[alpha-chloro-alpha-(2-thienyl)]methylidene-2,6-di(tert-butyl)-2,5-cyclohexadien-1-one (from Example 13) was added, with stirring a mixture of 5 ml of pyrrolidine and 50 ml of cold (0° C.) diethyl ether. After 10 minutes the mixture was diluted with diethyl ether and petroleum ether and then washed six times with water until the washings were no longer basic. The organic fraction was dried and then evaporated to provide a red solid which was recrystallized from a benzene-hexane mixture. Orange prisms of 2,6-di(tert-butyl)-4-[alpha-(1-pyrrolidino)-alpha-(2-thienyl)]methylidene-2,5-cyclohexadien-1-one, m.p. 193°–194° C. were obtained. Analysis: Calculated for $C_{23}H_{31}NOS$: %C, 74.7; %H, 8.5; %N, 3.8. Found: %C, 74.8, %H, 8.8; %N, 3.7. The structural assignment was confirmed by infrared and nuclear magnetic resonance spectral analysis.

EXAMPLE 15

Using the method of Example 14, 4-[alpha-chloro-alpha-(2-thienyl)]methylidene-2,6-di(tert-butyl)-2,5-cyclohexadien-1-one is reacted with morpholine to provide 2,6-di(tert-butyl)-4-[alpha-(1-morpholino)-alpha-(2-thienyl)]methylidene-2,5-cyclohexadien-1-one.

EXAMPLE 16

A solution of 0.6 g of 2,6-di(tert-butyl)-4-[alpha-(1-pyrrolidino)-alpha-(2-thienyl)]methylidene-2,5-cyclohexadien-1-one (from Example 14) in hexane was treated with dry hydrogen chloride gas to provide a precipitate which became a gum and subsequently hardened. Recrystallization was carried out by dissolving the precipitate in a minimum amount of isopropanol at 20° C. and diluting that solution with diethyl ether to the point that the solution just became cloudy. Crystals were separated by filtration to provide 0.5 g of light yellow crystals of 2,6-di(tert-butyl)-4-[alpha-(1-pyrrolidino)-alpha-(2-thienyl)]methylidene-2,5-cyclohexadien-1-one hydrochloride, m.p. 225°–227° C.

EXAMPLES 17–19

Using the method of Example 1, Parts A and B, the following intermediates of Formula VI may be prepared:

| Ex. No. | Starting Material of Formula II | Intermediate of Formula VI |
|---|---|---|
| 17 | 2,6-di(tert-butyl)-4-(5'-chloro-2'-thenoyl)phenol | (structure with Cl substituent on thiophene) |
| 18 | 2,6-di(tert-butyl)-4-(5'-methyl-2'-thenoyl)phenol | (structure with CH₃ substituent on thiophene) |
| 19 | 2,6-di(tert-butyl)-4-(3'-bromo-2'-thenoyl)phenol | (structure with Br substituent on thiophene) |

EXAMPLES 20-25

Using the method of Example 1, Part C, the following compounds of Formula I may be prepared by reaction of the indicated compound of Formula VI with the indicated amine:

| Ex. No. | Starting Material of Formula VI | Amine | Final Compound of Formula I |
|---|---|---|---|
| 20 | from Example 19 | piperidine | |
| 21 | from Example 19 | pyrrolidine | |
| 22 | from Example 19 | diethylamine | |
| 23 | from Example 20 | pyrrolidine | |
| 24 | from Example 20 | piperidine | |
| 25 | from Example 21 | pyrrolidine | 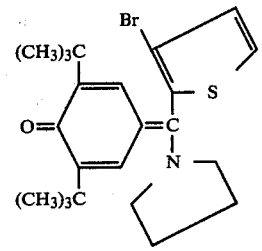 |

EXAMPLE 26

A mixture of 5.0 g (0.0158 mole) of 2,6-di(tert-butyl)-4-(2'-thenoyl)phenol and 3.5 g (0.17 mole) of phosphorus pentachloride in 25 ml of benzene was heated gently for 15 minutes and then heated at its reflux temperature for one hour until evolution of gas stopped. The mixture was then diluted with hexane and poured over ice. The organic phase was washed four times with cold water and once with saturated sodium chloride solution and was then dried over anhydrous sodium sulfate. The resulting organic solution containing 4-[alpha-chloroalpha-(2-thienyl)]methylidene-2,6-di(tert-butyl)-2,5-cyclohexadien-1one may be used directly for further reaction. The crude product obtained by evaporating the solvent was not stable. Stable product was obtained by chromatography over silica gel using carbon tetrachloride as the eluent.

EXAMPLE 27

To a mixture of 7.1 g (0.0225 mole) of 2,6-di(tert-butyl)-4-(2'-thenoyl)phenol in 150 ml of cold benzene was added gradually 10 ml of a 2.5 M butyl lithium solution, the temperature rising to 45° C. as the result of the addition. The mixture was allowed to cool, and 6 g of phosphorus pentachloride was then added gradually. The temperature rose to 35° C. as the result of the addition. The mixture was stirred, without heating, for one hour, at which time it was diluted with methylene chloride, washed with water and dried (over magnesium sulfate). Thin layer chromatography indicated the presence of 4-[alpha-chloro-alpha-(2-thienyl)]methylidene-2,6-di(tert-butyl)-2-5-cyclohexadiene-1-one which may be used for further reaction with an amine to provide an enamine in accordance with the present invention.

What is claimed is:

1. A compound of the formula

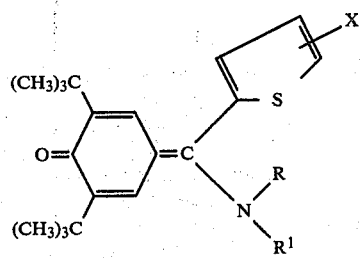

wherein R is lower alkyl; $R^1$ is selected from the group consisting of lower alkyl, benzyl and 2-(N,N-dimethylamino)ethyl; or R and R¹ are fused to form a five- or six-membered heterocyclic ring selected from the group consisting of pyrrolidinyl, piperidinyl, piperazinyl, N-lower alkyl piperazinyl, prolyl, morpholinyl, thiomorpholinyl, pyrrolyl, imidazolyl, and pyrazolyl, said ring optionally being substituted by a lower alkyl substituent; and X is hydrogen, methyl or halogen; or a pharmaceutically acceptable acid addition salt thereof.

2. A compound according to claim 1, wherein R is lower alkyl.

3. A compound according to claim 1, wherein R and R¹ are lower alkyl.

4. A compound according to claim 1, wherein R is methyl or ethyl and R¹ is methyl, ethyl or benzyl.

5. A compound according to claim 1, wherein R and R¹ are fused to form a five- or six-membered heterocyclic ring.

6. A compound according to claim 5, wherein the heterocyclic ring is pyrrolidinyl or piperidinyl.

7. The compound 2,6-di-tert-butyl-4-[(alpha-(1-piperidino)-alpha-2-thienyl]methylidene-2,5-cyclohexadien-1-one according to claim 1.

8. The compound 2,6-di-tert-butyl-4-[alpha-1-(pyrrolidino)-alpha-(2-thienyl)]methylidene-2,5-cyclohexadien-1-one according to claim 1.

9. The compound 2,6-di-butyl-4-[alpha-(N,N-dimethylamino)-alpha-(2-thienyl)]methylidene-2,5-cyclohexadien-1-one according to claim 1.

10. An antiinflammator composition, comprising and effective amount of at least one compound according to claim 1 and a pharmaceutically acceptable carrier.

11. A method for combatting inflammatory reactions in a mammal comprising delivering to the known or expected area of said mammalian body where said reaction has occured or is expected to occur, an effective amount of a composition according to claim 10.

12. A method according to claim 11, wherein said composition is administered orally.

13. A process for the preparation of an enamine of the formula

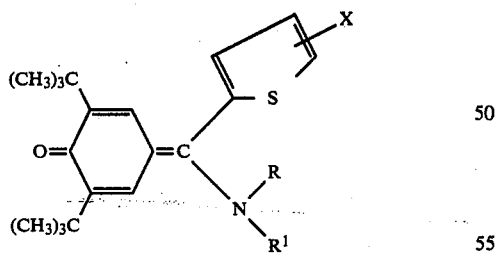

wherein R is lower alkyl; R¹ is selected from the group consisting of lower alkyl, benzyl, and 2-(N,N-dimethylamino)ethyl; or R and R¹ are fused to form a five- or six-membered heterocyclic ring selected from the group consisting of pyrrolidinyl, piperdinyl, piperazinyl, N-lower alkyl piperazinyl, prolyl, morpholinyl, thiomorpholinyl, pyrrolyl, imidazolyl, and pyrazolyl, said ring optionally being substituted by a lower alkyl substituent; and X is hydrogen, methyl or halogen, comprising the steps of (1) reacting a compound of the formula

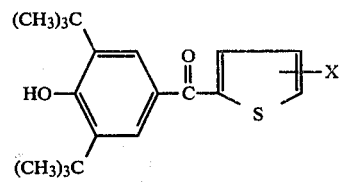

wherein X is defined as above, with a strong base to provide a metal salt of the formula:

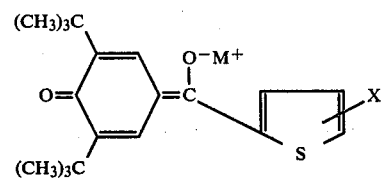

wherein X is as defined above and M is lithium, sodium or potassium;

(2) reacting said metal salt obtained in Step 1 with a chlorine source of the formula Cl—Q—Cl, wherein Q is

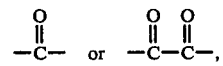

to provide a compound of the formula

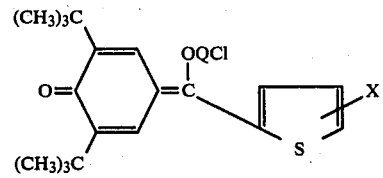

wherein X and Q are as defined above;

(3) heating the compound obtained in Step (2) to provide a compound of the formula

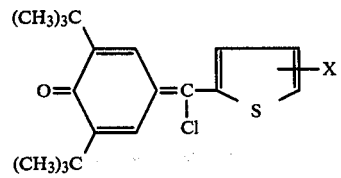

wherein X is as defined above; and (4) reacting the compound obtained in step (3) with an amine of the formula

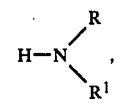

wherein R and R¹ are as defined above, to provide said enamine.

14. A compound of the formula

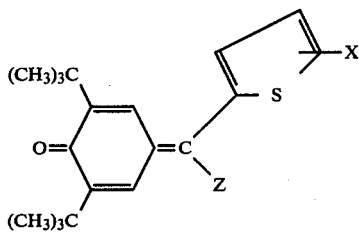

wherein X is hydrogen, methyl or halogen and Z is chlorine, —O⁻M⁺, or —OQCl, wherein M is lithium, sodium or potassium; and Q is

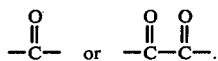

15. A compound according to claim 14, wherein Z is chlorine.

16. A process for the preparation of an enamine of the formula

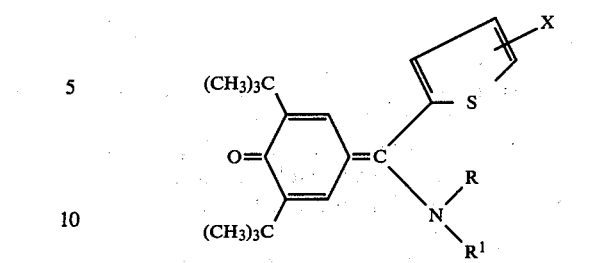

wherein R is lower alkyl; R¹ is selected from the group consisting of lower alkyl, benzyl, and 2-(N,N-dimethylamino)ethyl; or R and R¹ are fused to form an five- or six-membered heterocyclic ring selected from the group consisting of pyroolidinyl, piperidinyl, piperazinyl, N-lower alkyl piperazinyl, prolyl, morpholinyl, thiomorpholinyl, pyrrolyl, imidazolyl, and pyrazolyl, said ring optionally being substituted by a lower alkyl substituent; and X is hydrogen, methyl or halogen, comprising the step of reacting a compound of the formula

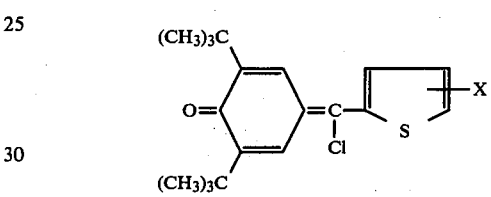

wherein X is as defined above with an amine of the formula

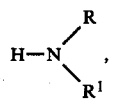

wherein R and R¹ are as defined above, to provide said enamine.

* * * * *